(12) United States Patent
Baltos et al.

(10) Patent No.: US 10,973,420 B2
(45) Date of Patent: Apr. 13, 2021

(54) THIN METAL MEMBRANE WITH SUPPORT

(71) Applicant: Heraeus Deutschland GmbH & Co. KG, Hanau (DE)

(72) Inventors: Nicholas Baltos, Maple Grove, MN (US); Oliver Keitel, Aschaffenburg (DE); Lena Weber, Alzenau (DE); Andreas Reisinger, Alzenau (DE)

(73) Assignee: HERAEUS DEUTSCHLAND GMBH & CO. KG, Hanau (DE)

( * ) Notice: Subject to any disclaimer, the term of this patent is extended or adjusted under 35 U.S.C. 154(b) by 0 days.

(21) Appl. No.: 16/692,343

(22) Filed: Nov. 22, 2019

(65) Prior Publication Data

US 2020/0093381 A1 Mar. 26, 2020

Related U.S. Application Data

(62) Division of application No. 14/653,340, filed as application No. PCT/EP2013/077000 on Dec. 17, 2013, now abandoned.

(30) Foreign Application Priority Data

Dec. 21, 2012 (DE) ...................... 10 2012 224 284.8

(51) Int. Cl.
*A61B 5/0215* (2006.01)
*B32B 15/01* (2006.01)
(Continued)

(52) U.S. Cl.
CPC .............. *A61B 5/0215* (2013.01); *B32B 1/00* (2013.01); *B32B 5/22* (2013.01); *B32B 15/00* (2013.01);
(Continued)

(58) Field of Classification Search
None
See application file for complete search history.

(56) References Cited

U.S. PATENT DOCUMENTS 5,364,586 A 11/1994 Trusov et al.
5,564,434 A 10/1996 Halperin et al.
(Continued)

FOREIGN PATENT DOCUMENTS

DE 10122889 A1 7/2003
DE 102005023699 A1 11/2006
(Continued)

OTHER PUBLICATIONS

Office Action dated Jul. 25, 2013 in DE Application No. 10 2012 224 284.8.
(Continued)

*Primary Examiner* — Jiong-Ping Lu
(74) *Attorney, Agent, or Firm* — Panitch Schwarze Belisario & Nadel LLP

(57) ABSTRACT

The present invention relates, generally, to a component containing a composite of at least two layers that are connected to each other, in which the first layer comprises a hole and the second layer has a thickness in the range of 1 to 50 μm. The first and second layers each contain at least one metal and compositions of the first and second layers are different. Further objects of the present invention include a method for producing a component containing at least two layers that are connected to each other and have the aforementioned features, a method for producing a component containing at least three layers that are connected to each other and have the aforementioned features, as well as a component that is obtained by one of the aforementioned methods and a device containing at least one of the aforementioned components for use in a living body.

2 Claims, 8 Drawing Sheets

(51) Int. Cl.
*C23F 1/44* (2006.01)
*B81C 1/00* (2006.01)
*B32B 1/00* (2006.01)
*B32B 5/22* (2006.01)
*B32B 15/04* (2006.01)
*B32B 15/18* (2006.01)
*B32B 15/00* (2006.01)
*B32B 15/20* (2006.01)
*A61B 5/024* (2006.01)

(52) U.S. Cl.
CPC ............ *B32B 15/01* (2013.01); *B32B 15/018* (2013.01); *B32B 15/04* (2013.01); *B32B 15/18* (2013.01); *B32B 15/20* (2013.01); *B81C 1/00158* (2013.01); *B81C 1/00436* (2013.01); *C23F 1/44* (2013.01); *A61B 5/02444* (2013.01); *A61B 2562/0247* (2013.01); *A61B 2562/12* (2013.01); *B81B 2201/0264* (2013.01); *B81B 2203/0127* (2013.01); *Y10T 428/12361* (2015.01); *Y10T 428/12493* (2015.01); *Y10T 428/12771* (2015.01)

(56) References Cited

U.S. PATENT DOCUMENTS

| | | | |
|---|---|---|---|
| 5,782,638 | A | 7/1998 | Warren, III et al. |
| 6,475,170 | B1 | 11/2002 | Doron et al. |
| 7,322,100 | B2 | 1/2008 | Jager et al. |
| 2002/0020298 | A1 | 2/2002 | Drost et al. |
| 2002/0028345 | A1 | 3/2002 | Kempf et al. |
| 2004/0247927 | A1 | 12/2004 | Kurz |
| 2006/0247539 | A1 | 11/2006 | Schugt et al. |
| 2007/0251389 | A1 | 11/2007 | Katsir et al. |
| 2009/0145630 | A1* | 6/2009 | Watanabe ............... H05K 1/116 174/251 |
| 2013/0060139 | A1 | 3/2013 | Richter et al. |
| 2014/0009035 | A1 | 1/2014 | Toyoda |

FOREIGN PATENT DOCUMENTS

| | | |
|---|---|---|
| EP | 0488229 A2 | 6/1992 |
| EP | 1114985 A1 | 7/2001 |
| WO | 9721986 A1 | 6/1997 |
| WO | 2006125691 A1 | 11/2006 |
| WO | 2012131911 A1 | 10/2012 |

OTHER PUBLICATIONS

Int'l Search Report and Written Opinion dated May 8, 2014 in Int'l Application No. PCT/EP2013/077000.

Office Action dated Aug. 21, 2017 in U.S. Appl. No. 14/653,340 by Baltos.

Office Action dated Nov. 15, 2017 in U.S. Appl. No. 14/653,340 by Baltos.

Office Action dated Jul. 5, 2018 in U.S. Appl. No. 14/653,340 by Baltos.

Office Action dated Feb. 5, 2019 in U.S. Appl. No. 14/653,340 by Baltos.

Office Action dated Jun. 24, 2019 in U.S. Appl. No. 14/653,340 by Baltos.

* cited by examiner

THIN METAL MEMBRANE WITH SUPPORT

CROSS-REFERENCE TO RELATED APPLICATIONS

This application is a Divisional of U.S. patent application Ser. No. 14/653,340, filed Jun. 18, 2015, which is a Section 371 of International Application No. PCT/EP2013/077000, filed Dec. 17, 2013, which was published in the German language on Jun. 26, 2014 under International Publication No. WO 2014/095940 A1, which claims priority under 35 U.S.C. § 119(b) to German Application No. 10 2012 224 284.8, filed Dec. 21, 2012, the disclosures of which are incorporated herein by reference.

BACKGROUND OF THE INVENTION

Membranes having a low membrane thickness maybe used as transmission media for pressure sensors in implantable devices or in medical instruments to be inserted into the human body for measurements and other activities. Generally, the pressure differences encountered inside the body are relatively low. For this reason, it is necessary to use membranes that are as thin as possible. This enables the transmission of pressure, and therefore the pressure measurement, to be accurate. Moreover, all materials that are used in this context and contact body fluids must be biocompatible.

Membranes of this type are known. Both metallic and plastic-based membranes are currently in use as materials. Conventionally, very thin metallic membranes are produced by abrading production methods, for example by milling or erosion. However, such membranes are not as thin as needed. Further, if membrane thicknesses of less than 50 µm are to be attained with these methods, a substantial effort is required in order to achieve homogeneous quality.

According to another known production method, a thin sheet of metal or metal foil of the desired thickness is used via a weld connection. It is feasible in this way to produce metal sheets and metal foils with low layer thicknesses. However, thus far there has been no method available for connecting these sheet metals or foils to a base body that would guarantee an airtight weld connection and homogeneous quality at acceptable prices.

A soldering procedure as an alternative to welding would be conceivable. However, this is disadvantageous in that further metals and alloys would need to be incorporated in addition to the participating metals. These alloys often have very limited biocompatibility. Moreover, this procedure bears the risk of forming local elements, which is associated with corrosion.

A production method for silicon membranes is known from micro system technology, a field that is distant from the production of biocompatible objects. Such silicon membranes are used as flow sensors. The membranes are produced by selective etching of the silicon wafer. The following documents are cited as pertinent examples: DE 10 2005 023 699 A1, EP 1 114 985 A1, and WO 1997/21986 A1. The cited methods apply dry etching with hydrogen chloride gas, which is common in the semiconductor industry. This approach is limited to silicon wafers and cannot be applied to the production of implantable membranes.

BRIEF SUMMARY OF THE INVENTION

Accordingly, the present invention is based on the object to provide an implantable component comprising a preferably metallic substrate and a metallic membrane, wherein the layer thickness of the membrane is as low as possible.

It is another object of the present invention to provide a metallic membrane wherein the layer thickness of the membrane is less than 50 µm, preferably less than 30 µm, or less than 10 µm.

It is another object of the present invention to provide a component in which a substrate and a membrane are connected at the contact surfaces in a two-dimensional manner, in particular in a liquid- and air-tight manner.

It is another object to provide a metal membrane that is connected to the substrate in a pressure-tight manner and, if applicable, with a component accommodating the membrane.

It is another object to provide a metal membrane that is suitable for transmitting pressure changes from one side of the metal membrane to the other side of the metal membrane.

It is another object to provide a production method for obtaining an implantable component comprising a preferably metallic substrate and a metallic membrane, wherein the layer thickness of the membrane is as low as possible, in particular less than 50 µm.

It is another object to provide a production method that is as simple and inexpensive as possible.

It is another object of the present invention to provide a component that may be used in medical devices that may be implanted in a body.

It is another object of the present invention to provide a method for producing components that solve one, and preferably all, of the objects specified above.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTIONS

Figure 1:
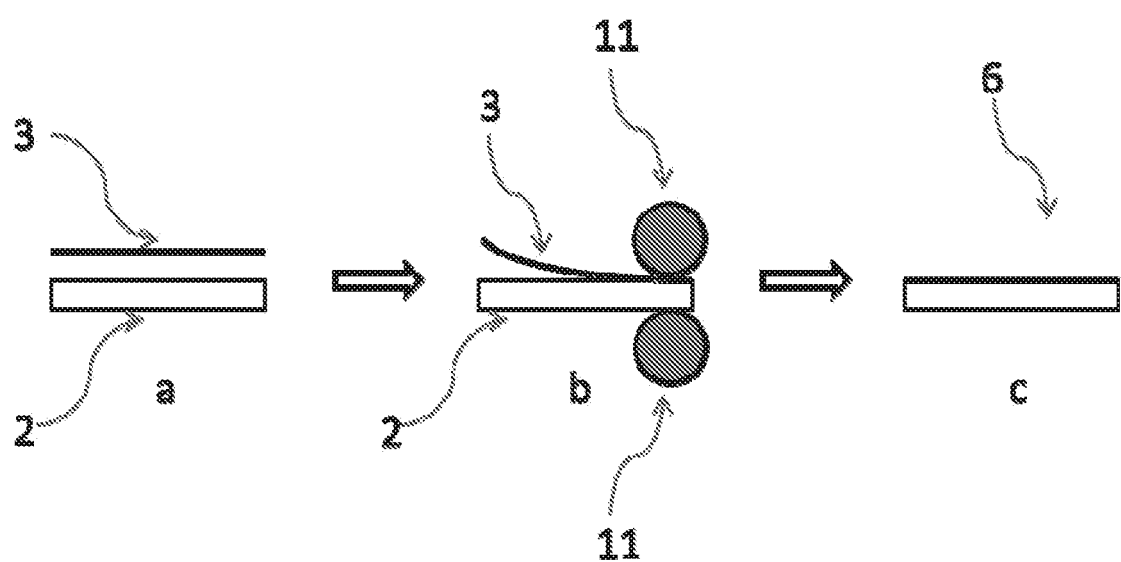
FIG. 1 shows a process for producing a composite according to one embodiment of the invention.

The present invention generally relates to a component comprising a composite of at least two layers that are connected to each other. The first layer comprises a hole and the second layer has a thickness in the range of 1 to 50 μm. The first and second layers each comprise at least one metal and the compositions of the first and second layers are different. The present invention is also directed to a method for producing a component comprising at least two layers that are connected to each other and have the aforementioned features, a method for producing a component comprising at least three layers that are connected to each other and have the aforementioned features, as well as a component that is obtained by one of the aforementioned methods and the use of at least one of the aforementioned components in a living body or for producing an implant for use in a living body.

A contribution to solving the aforementioned objects is made by a component, in particular a membrane, comprising a composite of at least two layers that are connected to each other. In the composite, the first layer comprises at least one hole, the second layer has a thickness in the range of 1 to 50 μm, preferably of 1 to 40 μm, or of 1 to 30 μm, or of 1 to 15 μm, the first layer and the second layer each comprises at least one metal, and the compositions of the first and second layers are different.

In the spirit of the present application, a hole may be understood to be a region of a layer where the layer is discontinuous throughout its entire thickness. The hole is bordered in the plane of the layer by a margin made of layer.

In the spirit of the present application, the term continuous may be understood to mean that the object thus specified or the region of a layer thus specified does not contain a hole, a gap of materials or the like. An object specified as being continuous may comprise variations in thickness if the thickness is always larger than zero.

The thickness of the layer is the extension of that layer perpendicular to a plane that may be placed in the layer at the measuring location. If the measurement of the thickness of a layer at multiple locations yields different values, the thickness is the arithmetic mean of the measured values. If the layer forms a tube, the tangential plane at the measuring location on the tube may be understood to be the plane in the layer.

In the spirit of the present invention, the term impervious may be understood to mean that a liquid, in particular water, or a gas, in particular helium, cannot pass through the object specified as being impervious at a pressure applied to the object in the range of 0 to 30,000 Pa. The imperviousness is measured by means of a tightness test of the object with helium (so-called "helium leakage test") according to the MIL-STD-883H standard, method 1014.13, test condition $A_4$.

In the spirit of the present invention, the term resistant may be understood to mean that a mass of an object specified as being resistant that is in contact with a substance does not decrease during the time of contact. In the spirit of the present invention, this is the case if the mass of the object after contact with the substance is less than 0.1% less than before contact with the liquid. Preferably, the mass increases or takes when it is in contact with another substance.

In the context of the present invention, the term biocompatible may be understood to mean that the object referred to as being biocompatible meets the pertinent biocompatibility requirements according to the ISO 10993 part 1-20 standard.

Non-precious metals are characterized by having a standard potential $E°$ (T=25° C., p=1.013 bar) of less than 0 V.

Preferably, the at least two layers of the component according to the invention that are connected to each other, i.e., the first layer and the second layer, form a membrane. A membrane of this type is used, for example, in devices for measuring a pressure difference, for example of a blood pressure in a human or in an animal. Specifically, the two layers that are connected to each other and the component according to the invention are suitable for determining a pressure difference of up to 25,000 Pa. In the context of the present invention, a pressure difference may be understood to mean that a relative pressure or pressure change, rather than an absolute pressure, is being measured.

The first layer according to the invention may comprise any shape that is suitable for connecting to the second layer and may consist of any material that is suitable for connecting to the second layer. The first layer and the second layer form a 2-dimensional composite, whereby the first layer contains one hole or multiple holes in the region of the surface superimposed by the second layer. In the component according to the invention, the first layer is preferably provided as a substrate and the second layer is preferably provided as a membrane. The composite of first and second layers is impervious with respect to gases or liquids, and is preferably impervious with respect to gases and liquids.

A combination of a hole in the first layer and a superimposed continuous second layer forms a membrane in which the first and second layers are connected in a continuous manner at the boundaries of the hole with respect to the first layer. In this context, the first layer forms a support for the membrane. This support may be shaped, for example, as a frame or as a grid.

For functioning as a membrane, the second layer has no holes, at least in those regions that are superimposed over one or more holes in the first layer. However, there may be other regions of the component in which a hole in the layer is superimposed with a hole in the second layer. Other regions of this type do not form a membrane and may, for example, serve for assembly of the composite of the first layer and second layer in the component.

In a preferred embodiment, the first layer of the component has a thickness in the range of 50 to 500 μm, preferably of 70 to 350 μm, or of 90 to 200 μm. The thickness of this layer may be determined by common measuring methods, in particular with a micrometer measuring screw.

In a preferred embodiment, the second layer of the component has a thickness in the range of 2.0 to 25 μm, preferably of 3 to 15 μm. The thickness of this layer may also be determined by common measuring methods, in particular on a transverse section of the layer by scanning electron microscopy.

The material of the first layer comprises at least one metal. In principle, all metals that are known to and are deemed well-suited for the intended purpose by a person skilled in the art are conceivable.

According to the invention, the composition of the first layer differs from the composition of the second layer. The compositions of the first layer and of the second layer are selected appropriately such that the composition of the first layer may be chemically removed by treatment with a liquid CA, whereas the composition of the second layer is resistant to this liquid CA at least for the duration of treatment of the first layer with the liquid CA.

In order to attain the aforementioned effects, the liquid CA may be appropriately selected such that the electrochemical potential of the liquid CA is larger than the electrochemical potential of the composition of the first layer at the surface of contact to the liquid CA. Moreover, the liquid CA is selected appropriately such that the electrochemical potential of the liquid CA is smaller than the electrochemical potential of the composition of the second layer at the surface of contact to the liquid CA. The electrochemical potentials of the compositions of the first, second and, if applicable, further layers and of the liquid CA during the treatment may be calculated by means of the Nernst equation (Roempp-Lexikon Chemie, 10th ed. (1998), volume 4, page 2869, entry "Nernstsche Gleichung" (Nernst equation)). The standard potentials E° (at T=25° C., p=1.013 bar) used in the Nernst equation may be looked up in tables or in the so-called electrochemical voltage series (CRC Handbook of Chemistry and Physics, 93rd Edition, 2012-2013, Section 5, Subsection "Electrochemical Series").

If a non-noble metal is included in a composition of a layer, the electrochemical potential of the metal and of the composition containing the metal may deviate from the aforementioned theoretical values. The non-noble metal behaves like a metal with a more positive E value than would be expected from its electrochemical potential. This phenomenon is called passivation. The potential of the passivated metal is called passivation potential. A passivation potential may arise in the case of a non-noble metal if a non-noble metal contacts water, air, liquid CA or a combination of two or more thereof. A continuous firmly-adhering passive layer made of an oxide or hydroxide of the non-noble metal is then formed at the contact surface. The passive layer at the surface of contact to a liquid CA affects the passivation potential. This passivation potential must be attained in order to be able to chemically remove the layer of metal situated underneath the passive layer in order to first remove the passive layer and then the metal of the metal layer. During the chemical removal of a metal, parts of the metal are preferably dissolved and abraded by oxidation from the metal body, for example a metal layer. According to the description above, a contact surface is the surface of a layer that contacts the liquid CA when this layer is treated with a liquid CA. According to the description above, the passivation potential is the electrochemical potential of a layer at the contact surface. Accordingly, a composite of at least two layers that are connected to each other is preferred, in which the electrochemical potential of the first layer at its surface of contact to a liquid CA is smaller than the electrochemical potential of the second layer at its surface of contact to the liquid CA.

Another option for selecting a suitable liquid CA for a given composite of first and second layers is to perform dissolution experiments. For this purpose, a liquid in consideration for the liquid CA is applied to weighed samples of the first and second layers and allowed to act for a period of time at treatment conditions (temperature, applied electrical voltage). Subsequently, the liquid is removed and the samples are weighed again. The liquid is deemed suitable as liquid CA if a decrease in weight due to the treatment with a liquid is noted in the sample of the first layer, whereas no decrease in weight is noted in the sample of the second layer.

In a preferred embodiment, the at least one metal of the first layer of the component is selected from the group consisting of silver, gold, platinum, titanium, iridium, niobium, tantalum, tungsten, palladium, copper, iron, steel, and stainless steel, in as far as suitable for medical implants, such as, e.g., 316L and 304, or a combination of at least two thereof. If multiple metals are present in the first layer as a combination, the combination is preferred to be an alloy. Preferred alloys for the first layer are alloys including niobium and tantalum; nickel and titanium; or platinum and iridium. Preferably, one or more further metals may be present in the aforementioned alloys. These further metals may be those from the list specified above or others that have not been specified above.

In a preferred embodiment, the at least one metal of the second layer is selected from the same metals from the same group, except for copper and iron, as the at least one metal of the first layer. If multiple metals are present as a combination, the combination is preferred to be an alloy; the alloys specified for the first layer are also preferred in this case. It is also preferred that this alloy contains one or more further metals. These further metals may be those from the list specified above or others that have not been specified above.

In a further embodiment, the metal or metals of the first layer differ from the metal or metals of the second layer.

Any and all liquids known to a person skilled in the art and deemed to be suitable for chemical removal of the first layer without removing the second layer may be used as liquid CA. In particular, liquid pure substances, mixtures of multiple pure substances or mixtures of one or more pure substances and one or more inorganic or organic solvents are conceivable as liquid CA. A person skilled in the art is aware of suitable liquids CA for combinations of first layer and second layer selected by the person skilled in the art.

Examples of preferred combinations of compositions of the first layer, compositions of the second layer, and the liquid CA are as follows:

|     | Composition of the first layer | Composition of the second layer | Ingredients of the liquid CA |
| --- | --- | --- | --- |
| (a) | Niobium | Platinum | HF/HNO$_3$/H$_2$O at a volume ratio of 1:1:3; or NaOH$_{conc.}$ |
| (b) | Gold | Platinum | KCN/H$_2$O (10 wt.-% KCN); or HCl/HNO$_3$ at a molar ratio of 3:1; or KI/I$_2$/H$_2$O at a molar ratio of 4:1:40 |
| (c) | Gold | Niobium | KCN/H$_2$O (10 wt.-% KCN); or HCl/HNO$_3$ at a molar ratio of 3:1; or KI/I2/H$_2$O at a molar ratio of 4:1:40 |
| (d) | Titanium | Platinum | HF/H$_2$O$_2$/H$_2$O at a molar ratio of 1:1:20 |

The aforementioned ingredients of the liquid CA are present, for example, as follows: HF: 48 wt.-%, water added up to 100 wt.-%; HNO$_3$: 69 wt.-%, water added up to 100 wt.-%; HCl: 36 wt.-%, water added up to 100 wt.-%; H$_2$O$_2$: 30 wt.-%, water added up to 100 wt.-%. The chemicals specified in the table maybe procured, for example, from Merck KGaA, D-64293 Darmstadt, Germany.

In a preferred embodiment, the compositions of the first layer and second layer are biocompatible.

In a different preferred embodiment, at least the side of the second layer facing away from the first layer is provided with a material that is biocompatible. In this case, the first layer may be made, at least in part, from one or more non-biocompatible materials; the same applies to coatings or devices that are arranged on the side of the first layer facing away from the second layer. The side of the second layer facing away from the first layer is often referred to as the external side of the membrane or of the component.

In a further preferred embodiment, a diffusion layer is arranged in the composite, between the first and second layers of the component. A diffusion layer may be understood to be a region between the first and second layers that comprises metals, in particular metal atoms, of the composition of the first layer as well as metals, in particular metal atoms, of the composition of the second layer. Usually, the diffusion layer has a gradient of each of the ingredients that are present in the diffusion layer. The diffusion layer between the first and second layers in the composite is considered to be the region in which the concentration comprises less than 98 wt.-%, relative to the sample, of metal, in particular metal atoms, of the composition of the first layer or of metal, in particular metal atoms, of the composition of the second layer or both. The presence of a diffusion layer may be tested, for example, by preparing a transverse section through the composite and by analyzing the surface of the transverse section by a combination of scanning electron microscopy and energy-dispersive x-ray analysis (also referred to as: SEM/EDX).

The first and second layers maybe connected to each other by their entire surfaces by any techniques that are known to a person skilled in the art and deemed to be suitable. Particularly preferably, the first and second layers of the component are joined by means of one of the following connecting techniques: cold welding, cladding, in particular roll cladding such as cold roll cladding, warm roll cladding or explosion cladding. The formation of diffusion layers may be effected, in particular, during warm roll cladding. In cold roll cladding and explosion cladding, the formation of diffusion layers may be effected through a thermal treatment after the cladding step. A combination of two or more of the aforementioned connection techniques is preferred as well.

In a further preferred embodiment, the component comprises a composite made of three connected layers, in which a third layer is arranged on the side of the first layer facing away from the second layer and comprises at least one hole so that each hole of the first layer has a hole of the third layer superimposed on it.

According to a preferred embodiment, the third layer comprises a thickness of more than 1 µm, of more than 2 µm, or of more than 5 µm. Often, the thickness of the third layer is in the range of 1 to 50 µm, preferably of 1 to 40 µm, or of 1 to 30 µm, or of 1 to 15 µm, or of 2 to 15 µm, or of 5 to 20 µm. From a functional point of view, the third layer should be at least thick enough such that the layer does not comprise any through-going gaps due to voids or other defects of the material.

On principle, all layers that are known to a person skilled in the art and deemed to be suitable for the intended purpose and contain at least one metal and differ from the composition of the first layer may be used as the third layer. Preferably, the at least one metal of the third layer is selected from the same group as the at least one metal of the second layer. In a further preferred embodiment, the at least one metal of the third layer and the at least one metal of the second layer are identical. In a further preferred embodiment, the compositions of the third layer and the composition of the second layer are identical.

A method for producing a component comprising a composite of at least two layers that are connected to each other is a further object of the present invention. The second layer has a thickness in the range of 1 to 50 µm; the first and second layers each comprises at least one metal; the third layer has a thickness of at least 1 µm; and the compositions of the first and second layers are different. The method comprises at least the following process steps:

(i) providing, superimposing, and connecting the first and second layers while forming a composite;

(ii) applying a coating SL onto a part of the first layer;

(iii) contacting parts of the first layer not provided with the coating to a liquid, causing at least a part of the first layer to be removed and at least one hole to be formed in the first layer;

(iv) optionally removing the coating SL from the first layer; and (vi) optionally splitting-up the composite; to obtain the component.

Objects that have been described above in the context of the inventive component may be used, according to the invention and preferably, if applicable, as the first layer and as the second layer. Moreover, the component obtained according to the inventive method may contain a diffusion layer or further preferred features that have been described above with respect to the inventive component. Moreover, a component obtained according to the inventive method may preferably contain more than one of the preferred features described above.

According to process step (i), the first and second layers are each provided, superimposed, and connected to each other while forming a composite. The inventive method may be run as a continuous or as a discontinuous process. Referring to a continuous process, the first layer and the second layer are preferably provided from a stock, e.g., a roll each, and fed to the superimposing and then to the connecting. Preferably, the superimposing and the connecting may proceed simultaneously in this context. Referring to a discontinuous process, for example, a plate of the first layer and a plate of the second layer are each first taken from a stock. Subsequently, the surfaces of the two plates are superimposed, at least partially, and the plates are then fed to the connecting.

The first and second layers may be connected to each other by any techniques that are known and are deemed to be suitable by a person skilled in the art. Preferably, the connecting is effected on the entire surface in the region in which the two layers are superimposed. Particularly preferably, the connecting of the first and second layers to form a composite is effected through one of the following connecting techniques: cold welding, cladding, in particular explosion cladding or roll cladding, such as cold roll cladding or warm cladding. The formation of diffusion layers may be effected, in particular, during warm roll cladding. In cold roll cladding and explosion cladding, the formation of diffusion layers may be effected through a thermal treatment after the cladding step. A combination of two or more of the aforementioned connecting techniques is preferred as well.

In step (ii) of the inventive method, a coating SL is applied to at least a part of the first layer.

According to a preferred embodiment, the coating SL is resistant to the liquid CA. Any layer-forming agents, which, after forming the coating, are resistant to the selected liquid CA and adhere to the first layer, may be used for the coating SL. All coatings that are known to a person skilled in the art and are deemed suitable are conceivable as coating SL. These coatings SL are often referred to as protective lacquer, covering lacquer or masking agent. A shrinkable tubing is another preferred coating SL.

In a preferred embodiment, parts of the first layer are covered by a coating SL, for example a lacquer, in particular a covering lacquer or a so-called photoresist, prior to the application of the liquid.

A photoresist is a coating SL that is resistant to the chemicals used in the method according to the invention at least for a certain period of time, preferably permanently. Initially, a photoresist precursor is applied to the full surface or at least to part of the surface of the first layer and a lacquer is formed. Then, parts of the lacquer are exposed to radiation. The lacquer thus applied is then destroyed at the exposed sites by the irradiation and any residues of the destroyed lacquer are removed. The substrate treated according to the aforementioned alternative method is then subjected to the method according to the invention.

In a second alternative method, a photoresist precursor is being applied. However, the lacquer is formed only at the sites that are being exposed to radiation. Any non-fixed and/or non-cured photoresist precursor is then removed. The substrate treated according to the aforementioned alternative method is then subjected to the method according to the invention.

Preferred examples of a coating SL for the selected liquid CA are shown in the following table. This listing is not limiting.

|   | Liquid CA[2)] | Coating SL |
|---|---|---|
| a) | $HF/HNO_3/H_2O$ | Etching resist SD 2052AL[1)] |
| b) | $HCl/HNO_3/H_2O$ | Etching resist SD 2052AL[1)] |
| c) | $KCN/H_2O$ | Metal, e.g. platinum |
| d) | $NaOH_{conc.}$ | Metal, e.g. platinum |
| e) | $KI/I_2/H_2O$ | Etching resist SD 2052AL[1)] |

[1)]available from Lackwerke Peters GmbH & Co KG, D-47906 Kempen;
[2)]ingredients and mixing ratios as above.

In a preferred embodiment of the method according to the invention, at least a part of the first layer, or a part of the coating SL, or a part of both is removed by mechanical or electrical processing after step (i) and before step (ii). A part of the first layer or a part of the coating SL or a part of the first layer and of the coating SL applied to it may be removed by any and all methods that are known and are deemed to be suitable by a person skilled in the art. Mechanical abrasion methods, such as, for example, milling or spark erosion, are mentioned as methods that are preferred in this context. Irradiation of the coating SL with an energy-rich radiation source, for example a laser or X-rays, is a further preferred method for abrasion specifically of the coating SL.

Subsequently, parts of the first layer not provided with the coating are contacted to the liquid CA in step (iii) of the inventive method so that the contacting causes at least a part of the first layer to be removed and at least one hole to be formed in the first layer. The removal of the first layer at the sites made to contact the liquid CA is usually effected, as described above, by chemical processes, in particular by dissolution or oxidation processes. According to a preferred embodiment, an electrical potential is applied to the component, or to the liquid CA, or to both, in addition to removing the at least one part of the first layer. A current flow induced by the electric potential may accelerate the removal of the first layer. Step (iii) is completed by removing the liquid CA, for example by wiping off the liquid CA, and, if applicable, by removing the electrical potential. Optionally, water or an organic solvent may be used for rinsing.

According to a preferred embodiment, the coating SL is removed from the remaining parts of the first layer in a step (iv) This may be done:
  (i) mechanically, for example by a polishing process, a grinding process or a milling process, or
  (ii) with a liquid, for example, with an alkaline solution,
  (iii) by irradiation, for example, as described above, or by a combination of at least two of the methods mentioned in items i to iii.

If a shrinkable tubing is selected for the coating SL, the removing is preferably effected by dissolving or cutting the shrinkable tubing and then pulling it off.

According to a further preferred embodiment, the composite obtained according to either one of the steps (iii) or (iv) is split-up into multiple parts in a step (v), whereby multiple components are thus obtained. If the component is not split-up into multiple parts, one component is obtained.

A method for producing a component comprising a composite of at least three layers that are connected to each other is a further object of the present invention, in which the second layer has a thickness in the range of 1 to 50 µm; the first layer, the second layer, and the third layer each comprise at least one metal; the third layer has a thickness of at least 1 µm; the compositions of the first and second layers are different; and the compositions of the first and third layers are different. The method comprises at least the following process steps:
  (i) providing, superimposing, and connecting the third layer, first layer, and second layer while forming a composite;
  (ii) removing a part of the third layer;
  (iii) contacting parts of the first layer not provided with the third layer to a liquid CA, causing at least a part of the first layer to be removed and at least one hole to be formed in the first layer;
  (iv) optionally removing the third layer; and
  (v) optionally splitting-up the composite; to obtain the component.

Objects that have been described above in the context of the inventive component and of the inventive method specified earlier may be used according to the invention and preferably, if applicable, as first and second layers. Moreover, the component obtained according to the present inventive method may contain one or more diffusion layer(s) or further preferred features that have been described above with respect to the inventive component or with respect to the inventive method specified earlier. Moreover, a component obtained according to the inventive method may preferably contain more than one of the preferred features described above.

On principle, all layers that are known to a person skilled in the art and are deemed to be suitable for the intended purpose and contain at least one metal and differ from the composition of the first layer may be used as the third layer. Preferably, the at least one metal of the third layer is selected from the same group as the at least one metal of the second layer. In a further embodiment, the at least one metal of the third layer and the at least one metal of the second layer are identical. In a further embodiment, the composition of the third layer and the composition of the second layer are identical.

According to process step (i), the third layer, the first layer, and the second layer each are provided, superimposed, and connected to each other while forming a composite. The inventive method may be run as a continuous or as a discontinuous process. Referring to a continuous process, the third layer, the first layer, and the second layer are preferably provided from a stock, e.g., a roll each, and fed to the superimposing and then to the connecting. Preferably, the superimposing and the connecting may proceed simultaneously in this context. Referring to a discontinuous process, for example, a plate of the third layer, a plate of the first layer, and a plate of the second layer each are first taken from a stock. Subsequently, the surfaces of the three plates are superimposed, at least partially, and the plates are then fed to the connecting.

The third layer, the first layer, and the second layer may be connected to each other by any and all techniques that are known and deemed to be suitable by a person skilled in the art. Preferably, the connecting is effected on the entire surface in the region in which at least two of the three layers are superimposed. Particularly preferably, the connecting of the three layers to form a composite is effected through one of the following connecting techniques: cold welding, cladding, in particular explosion cladding or roll cladding, such as cold roll cladding or warm cladding. The formation of diffusion layers may be effected, in particular, during warm roll cladding. In cold roll cladding and explosion cladding, the formation of diffusion layers may be effected through a thermal treatment after the cladding step.

In a preferred embodiment of the method according to the invention, at least a part of the third layer is removed by mechanical or electrical processing after step (i) and before step (ii). The removing of a part of the third layer may be effected according to any and all methods that are known and deemed to be suitable by a person skilled in the art. Mechanical abrasion methods, such as, for example, milling or spark erosion, are preferably selected methods.

Subsequently, parts of the first layer not provided with the third layer are contacted to a liquid CA in step (iii) of the inventive method. The contacting causes at least a part of the first layer to be removed and at least one hole to be formed in the first layer. The removal of the first layer at the sites made to contact the liquid CA is usually effected by chemical processes, in particular by dissolution or oxidation processes. According to a preferred embodiment, an electrical potential is additionally applied to the component or to the liquid CA or to both. A current flow induced by the electric potential may support the removal of the first layer. Step (iii) is completed by removing the liquid CA, for example, by wiping off the liquid CA, and, if applicable, by removing the electrical potential. Optionally, water or an organic solvent may be used for rinsing.

If multiple components are to be produced from a composite, the method described above is implemented appropriately such that multiple holes are formed.

According to another embodiment, the third layer is removed from the first layer at least partially, but preferably completely, in a step (iv). This is done mechanically, for example by means of a polishing process, a grinding process or a milling process.

According to a preferred embodiment, step (iv) is not implemented. In this case, the third layer remains on the first layer.

According to a further preferred embodiment, the composite obtained according to step (iii) or (iv) is split-up into multiple parts in a step (v) to obtain multiple components. If the component is not split-up into multiple parts, one component is obtained.

According to a further preferred refinement, the first layer, the second layer and, if applicable, the third layer are provided in the form of tubes. In this case, the superimposing is effected by inserting the tubes into each other in the desired sequence; the tubes may comprise one or more of the features described above with respect to the three layers. Referring to tubes, the composite made of at least two or at least three layers that are connected to each other is preferably attained by drawing the tubes. Drawing the tubes is associated with a reduction of the cross-section of the tubes, which leads to an intimate composite being obtained. Pertinent details are known to a person skilled in the art.

A component comprising a composite that is obtained according to either one of the two inventive methods described above is another object of the present invention.

A component comprising a composite as described above that is obtained according to either one of the inventive methods described above is another object of the present invention.

A device comprising the inventive component described above comprising a composite is another object of the present invention. Preferably, this device is selected from an implant, in particular a cardiac pacemaker, a probe, a pressure measuring device, in particular for measuring pressures in a human or animal body, e.g., a blood pressure measuring device.

A method for producing a device for use in a living body which comprises the inventive component described above is another object of the present invention. Preferably, this device is selected from an implant, in particular a cardiac pacemaker, a probe, a pressure measuring device for measuring pressures in a human or animal body, e.g., a blood pressure measuring device.

Referring to the figures, FIG. 1 shows a process for producing a composite 6 from two layers 2 and 3. This process may be run continuously or discontinuously. In step a, a first layer 2 and a second layer 3 are provided and superimposed. In step b, the two layers 2 and 3 are connected intimately by guiding them between rollers 11. The rolling reduces the thickness of the layers 2 and 3 (not shown here). The resulting composite 6 is shown in c.

Figure 2:
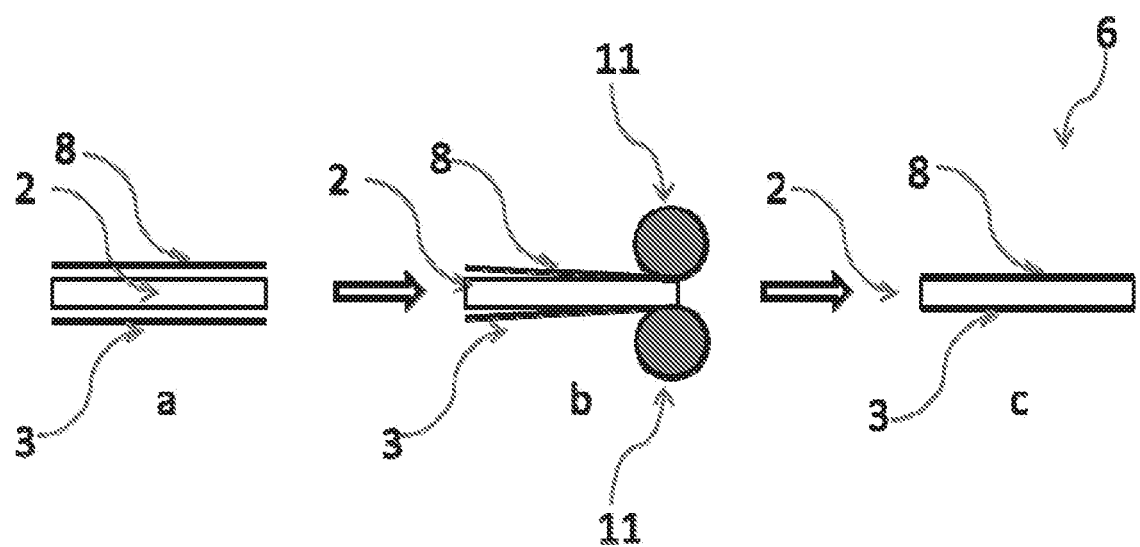
FIG. 2 shows a process for producing a composite according to a second embodiment of the invention.

FIG. 2 shows a process for producing a composite 6 made of three layers 2, 3, and 8. This process may also be run continuously or discontinuously. In step a, a third layer 8, a first layer 2, a second layer 3 are provided and superimposed. In step b, the three layers 8, 2, and 3 are connected intimately by guiding them between rollers 11. The rolling reduces the thickness of the layers 8, 2, and 3 (not shown here). The resulting composite 6 is shown in c.

Figure 3:
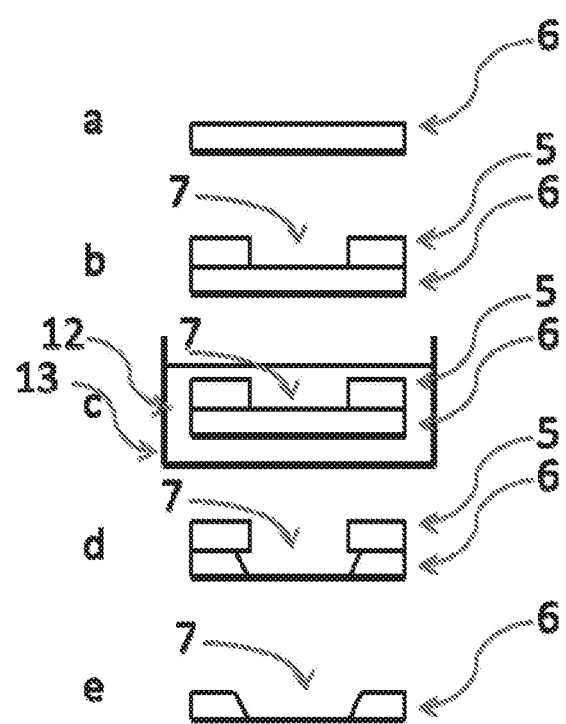
FIG. 3 shows a process for producing a component comprising a support layer and a membrane according to a further embodiment of the invention.

FIG. 3 shows a process for producing a component comprising a support layer and a membrane. Image a shows a composite 6 made of two layers 2 and 3 (not shown). This is coated with a coating SL 5. A hole 7 is formed in the coating SL 5 by removing a part of the coating SL 5.

In image b, the coating SL 5 now comprises a hole 7, which is subsequently immersed in a bath 13 of a liquid 12. Image c shows an arrangement in which the composite 6 with the hole 7 in the coating SL 5 is being treated with a liquid CA 12 in a bath 13. Afterwards, the liquid CA is removed, e.g., by rinsing. Image d shows the treated composite 6 which comprises a hole 7 that is present both in layer 5 and in layer 6. Image e shows the composite 6 after the coating SL 5 has been removed.

Figure 4:
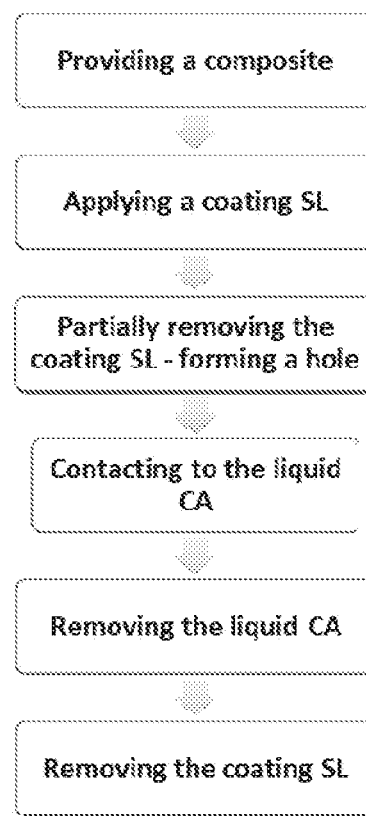
FIG. 4 is a flowchart corresponding to the process depicted in FIG. 3.

FIG. 4 is a flowchart corresponding to the process depicted in FIG. 3.

Figure 5:
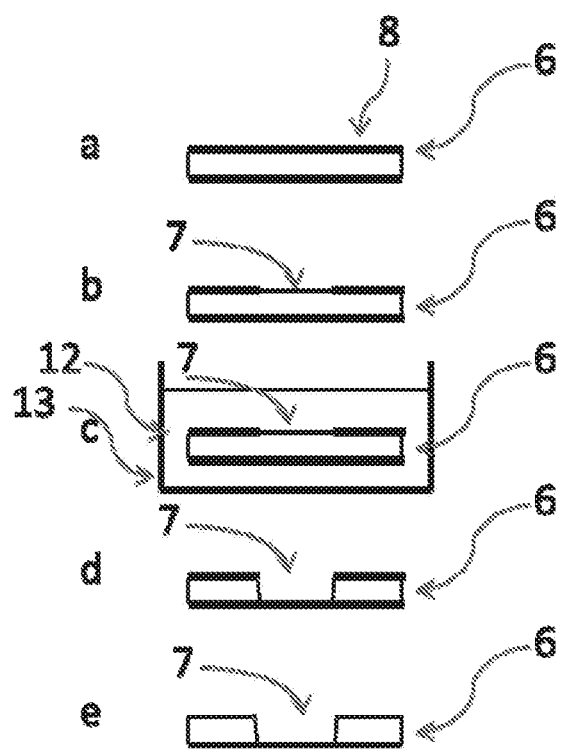
FIG. 5 shows another process for producing a component comprising a support layer and a membrane.

FIG. 5 shows another process for producing a component comprising a support layer and a membrane. Here, the composite consists of three layers, whereby the third layer 8 is resistant to the liquid CA. Image a shows the composite 6 made of three layers 2, 3 (both not shown), and 8.

A hole 7 is formed in the composite 6. In image b, the composite 6 comprises a hole 7, which is subsequently immersed in a bath 13 containing a liquid 12. Image c shows an arrangement in which the composite 6 with the hole 7 in layer 8 is being treated with a liquid CA 12 in a bath 13. Afterwards, the liquid CA is removed, e.g., by rinsing. Image d shows the treated composite 6 which comprises a hole 7 that is present both in layer 8 and in layer 6. Optionally, layer 8 is removed. Image e shows the composite 6 after layer 8 has been removed.

Figure 6:
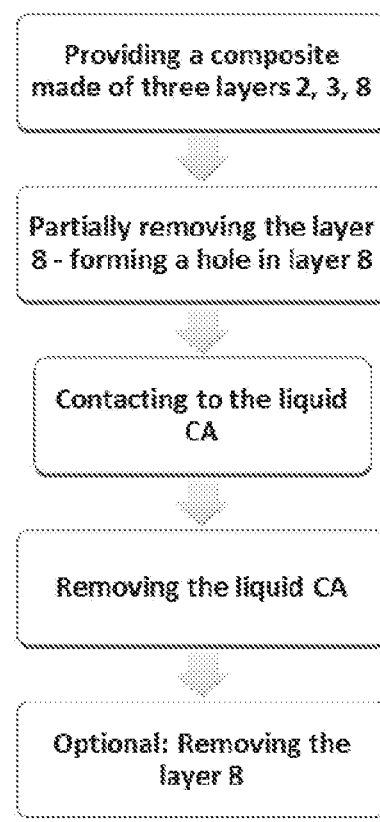
FIG. 6 is a flowchart corresponding to the process depicted in FIG. 5.

FIG. 6 is a flowchart corresponding to the process depicted in FIG. 5.

Figure 7:
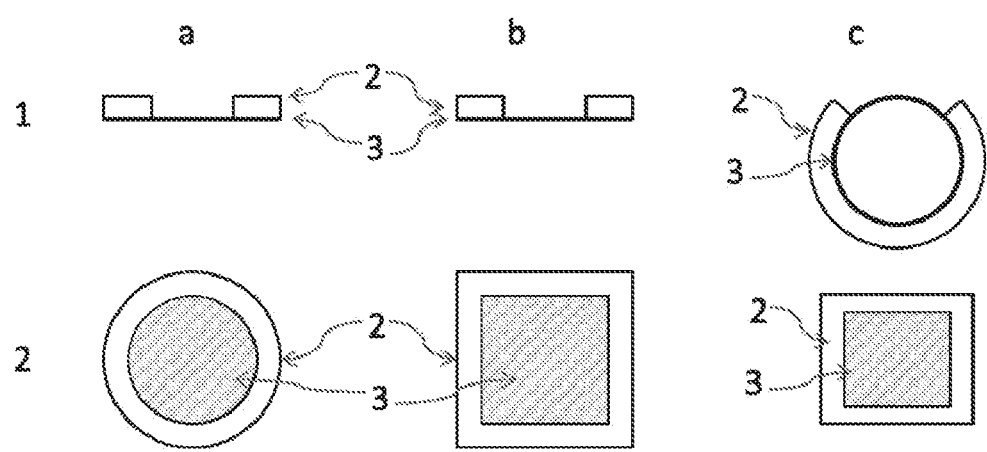
FIG. 7 shows examples of components according to embodiments of the invention, each comprising a composite made of two layers.

FIG. 7 shows examples of components according to embodiments of the invention, each comprising a composite made of two layers. Line 1 represents a cross-section each and line 2 represents a top view onto each component. FIG.

7a depicts a circular component with a planar membrane (second layer 3) and a cylindrical ring made of the first layer 2. FIG. 7b depicts a rectangular component with a planar membrane (second layer 3) and a rectangular frame made of the first layer 2. FIG. 7c shows a cylindrical component with a domed membrane as part of the second layer 3 that forms an internal cylinder and with a ring made of the first layer 2 forming an external cylinder.

Figure 8:
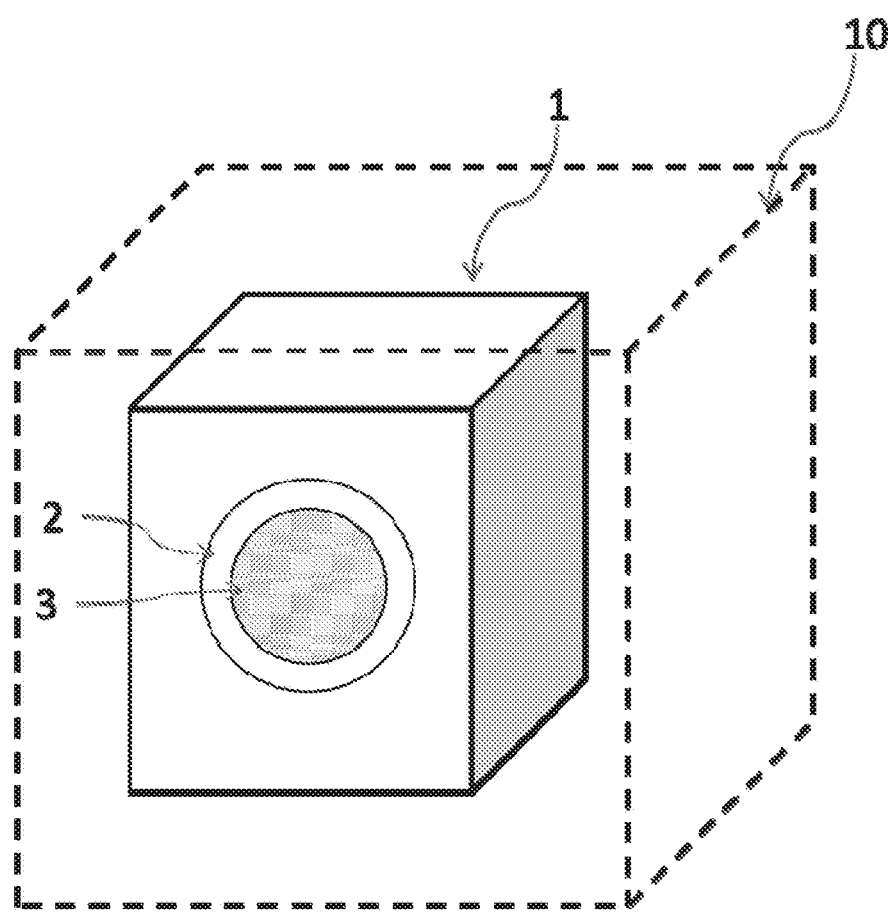
FIG. 8 shows a schematic of a device 10 according to an embodiment of the invention.

FIG. 8 is a diagram of a device 10 (shown dashed) comprising a component 1 with a composite made of a first layer 2 and a second layer 3.

The invention will now be described with reference to the following, non-limiting example.

EXAMPLE

Firstly, a cold-clad Nb/Pt sheet consisting of a niobium layer with a thickness of 194 µm and a platinum layer with a thickness of 6 µm (thickness specifications refer to the cold-clad Nb/Pt sheet; Nb/Pt sheet available from Vincent Metal Products, Inc., 33 Plan Way, Unit 3C, Warwick, R.I. 02886, USA) was cut into rectangular plates having a surface area of 8 mm×8 mm. The plate was coated appropriately on the niobium surface and on the narrow sides (these correspond to the surfaces along the thickness of the sheet plates) using etch resist SD2052 AL cover lacquer (available from Lackwerke Peters GmbH & Co. KG, D-47906 Kempen) such that a uniformly colored (blue) film was generated. Particular attention was paid to also carefully coating the edges of the niobium surface with lacquer. A field sized 2 mm×4 mm in the middle of the niobium surface of the plate was spared, i.e., was not covered with the lacquer. The coating was then treated for 30 minutes at 80° C. in a convection oven. Subsequently, a mixture of hydrofluoric acid (concentration HF=48 wt.-%, filled up to 100 wt.-%:water), nitric acid (concentration $HNO_3$=69 wt.-%, filled up to 100 wt.-%:water) (available from Merck KGaA, D-64293 Darmstadt, Germany) and deionized water (also demineralized water) at a ratio of 1:1:3 was prepared and the coated plate was placed in a bath of this mixture for 30 minutes at a temperature of 25° C. The niobium surface of the plate faced upwards in this context. After this treatment, the coated and treated plate was taken out of the bath and rinsed with deionized water. Subsequently, the lacquer coating of the plate was removed by immersing the plate in a bath of diluted sodium hydroxide. Then, deionized water was used to rinse again. Subsequently, this was rinsed again with ethanol. The treated plate comprised a continuous platinum layer and a niobium layer, in which the niobium layer had a hole that extended from the niobium surface of the plate to the platinum surface and was situated in the location in which the field with no lacquer coating previously had been.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for producing a component comprising a composite comprising at least a first layer and a second layer that are connected to each other,
   wherein the second layer has a thickness in the range of 1 to 50 µm;
   the first layer and the second layer each comprises at least one metal; and
   the compositions of the first layer and the second layer are different; the method comprising at least the following process steps:
   (i) providing, superimposing, and connecting the first layer and the second layer while forming a composite;
   (ii) applying a coating SL onto a part of the first layer; and
   (iii) contacting parts of the first layer not provided with the coating to a liquid CA, causing at least a part of the first layer to be removed and at least one hole to be formed in the first layer; thereby obtaining the component;
   wherein at least a part of the first layer is removed by mechanical or electrical processing after step (i) and before step (ii).

2. The method for producing a component according to claim 1, wherein the coating SL is resistant to the liquid CA, at least during step (iii).

* * * * *